(12) United States Patent
Zhang

(10) Patent No.: US 8,868,168 B2
(45) Date of Patent: Oct. 21, 2014

(54) SYSTEM FOR CARDIAC CONDITION CHARACTERIZATION USING ELECTROPHYSIOLOGICAL SIGNAL DATA

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 514 days.

(21) Appl. No.: 13/160,636

(22) Filed: Jun. 15, 2011

(65) Prior Publication Data

US 2012/0123285 A1    May 17, 2012

Related U.S. Application Data

(60) Provisional application No. 61/412,413, filed on Nov. 11, 2010.

(51) Int. Cl.
*A61B 5/0452* (2006.01)

(52) U.S. Cl.
CPC ........... *A61B 5/0452* (2013.01); *A61B 5/04525* (2013.01)
USPC ....................................................... 600/516

(58) Field of Classification Search
CPC .......................... A61B 5/0452; A61B 5/04525
USPC ....................................................... 600/516
See application file for complete search history.

(56) References Cited

U.S. PATENT DOCUMENTS

| | | | |
|---|---|---|---|
| 4,681,117 A | 7/1987 | Brodman | |
| 4,798,211 A | 1/1989 | Goor et al. | |
| 4,924,875 A | 5/1990 | Chamoun | |
| 4,930,075 A | 5/1990 | Kortas | |
| 5,054,496 A | 10/1991 | Wen et al. | |
| 5,159,932 A | 11/1992 | Zanetti et al. | |
| 5,365,426 A | 11/1994 | Siegel et al. | |
| 6,024,705 A | 2/2000 | Schlager et al. | |
| 6,112,116 A | 8/2000 | Fischell et al. | |
| 6,339,720 B1 | 1/2002 | Anzellini et al. | |
| 6,368,284 B1 | 4/2002 | Bardy | |
| 6,424,860 B1 | 7/2002 | Karlsson et al. | |

(Continued)

OTHER PUBLICATIONS

Stuart E Sheifer, et al., "Unrecognized Myocardial Infarction", Annals of Internal Medicine, Nov. 6, 2001, vol. 135, Issue 9, pp. 801-811.

(Continued)

*Primary Examiner* — Tammie K Heller
(74) *Attorney, Agent, or Firm* — Brennan K Bradley

(57) ABSTRACT

A system for heart performance characterization and abnormality detection includes an interface for receiving signal data representing an electrical signal indicating electrical activity of a patient heart over multiple heart beat cycles. A signal processor uses the received signal data in calculating at least one of, (a) a first signal characteristic value substantially comprising a ratio of a time interval from S wave to T wave, to a time interval from Q wave to S wave and (b) a second signal characteristic value substantially comprising a ratio of a T wave base voltage from a peak of a T wave to a zero base reference voltage, to an R wave base voltage from a peak of an R wave to a zero base reference voltage. A comparator compares at least one of the first and second characteristic values with a threshold value to provide a comparison indicator. A patient monitor in response to the comparison indicator indicating a calculated signal characteristic value exceeds the threshold value, generates an alert message associated with the threshold.

19 Claims, 6 Drawing Sheets

(56) References Cited

U.S. PATENT DOCUMENTS

| | | |
|---|---|---|
| 6,468,263 B1 | 10/2002 | Fischell et al. |
| 6,501,983 B1 | 12/2002 | Natarajan et al. |
| 6,882,883 B2 | 4/2005 | Condie et al. |
| 7,072,708 B1 | 7/2006 | Andresen et al. |
| 7,181,268 B2 | 2/2007 | Sheldon et al. |
| 7,225,015 B1 | 5/2007 | Min et al. |
| 7,231,244 B2 | 6/2007 | Laitio |
| 7,266,410 B2 | 9/2007 | Chen |
| 7,277,745 B2 | 10/2007 | Natarajan |
| 7,299,087 B2 | 11/2007 | Bardy |
| 7,361,473 B2 | 4/2008 | Valkirs et al. |
| 7,415,307 B2 | 8/2008 | Sharma et al. |
| 7,496,409 B2 * | 2/2009 | Greenhut et al. ............. 607/116 |
| 8,688,200 B2 * | 4/2014 | Song et al. .................... 600/509 |
| 2008/0082014 A1 * | 4/2008 | Cao et al. ...................... 600/509 |

OTHER PUBLICATIONS

S. Abbound, et al., "Detection of transient myocardial ischemia by computer analysis of standard and signal-averaged high-frequency electrocardiograms in patients undergoing percutaneous transluminal coronary angioplasty", Circulation, vol. 76, 585-596.

* cited by examiner

| Signal names | Signal function and morphology |
|---|---|
| $A_{R\_max}$ | Maximum magnitude (peak to peak) voltage value for R wave (usually also equal to the $A_{RS}$ (which is the magnitude voltage value from R wave to S wave) |
| $A_{R\_base}$ | R wave base voltage which is from the peak of R wave to the zero base reference |
| $A_{T\_base}$ | T wave base voltage which is from the peak of T wave to the zero base reference |
| $A_{QR}$ | The peak voltage difference from the peak of R wave to peak of the T wave |
| $A_{RT}$ | The peak voltage difference from the peak of R wave to peak of the T wave |
| $A_{T\_max}$ | Maximum magnitude (peak to peak) voltage value for T wave |
| $T_{QR}$ | The time duration from Q wave to R wave; this is name fast ventricular depolarization portion in the heart cycle; |
| $T_{RS}$ | The time duration from R wave to S wave; this is name slow ventricular depolarization portion in the heart cycle; |
| $T_{RT}$ | The time duration from R wave to end of T wave; |
| $T_{QS}$ | The tim e duration from Q wave to S wave; this is the main time for ventricular depolarization which is named as "contraction portion" in the whole heart beat |
| $T_{ST}$ | The time duration from S wave to T wave; this is the main time for ventricular Repolarization which is named as "perfusion portion" in the whole heart beat |

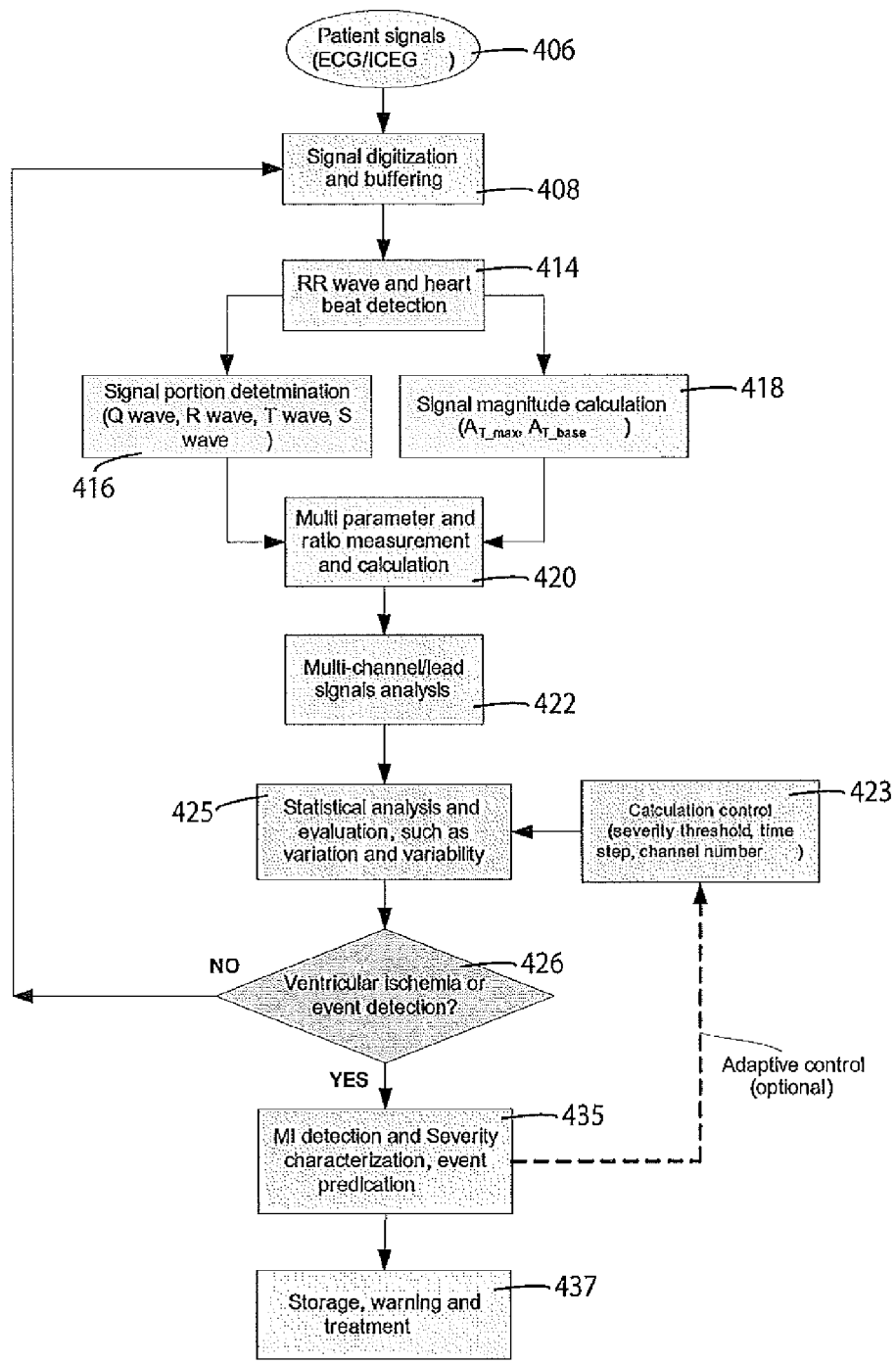

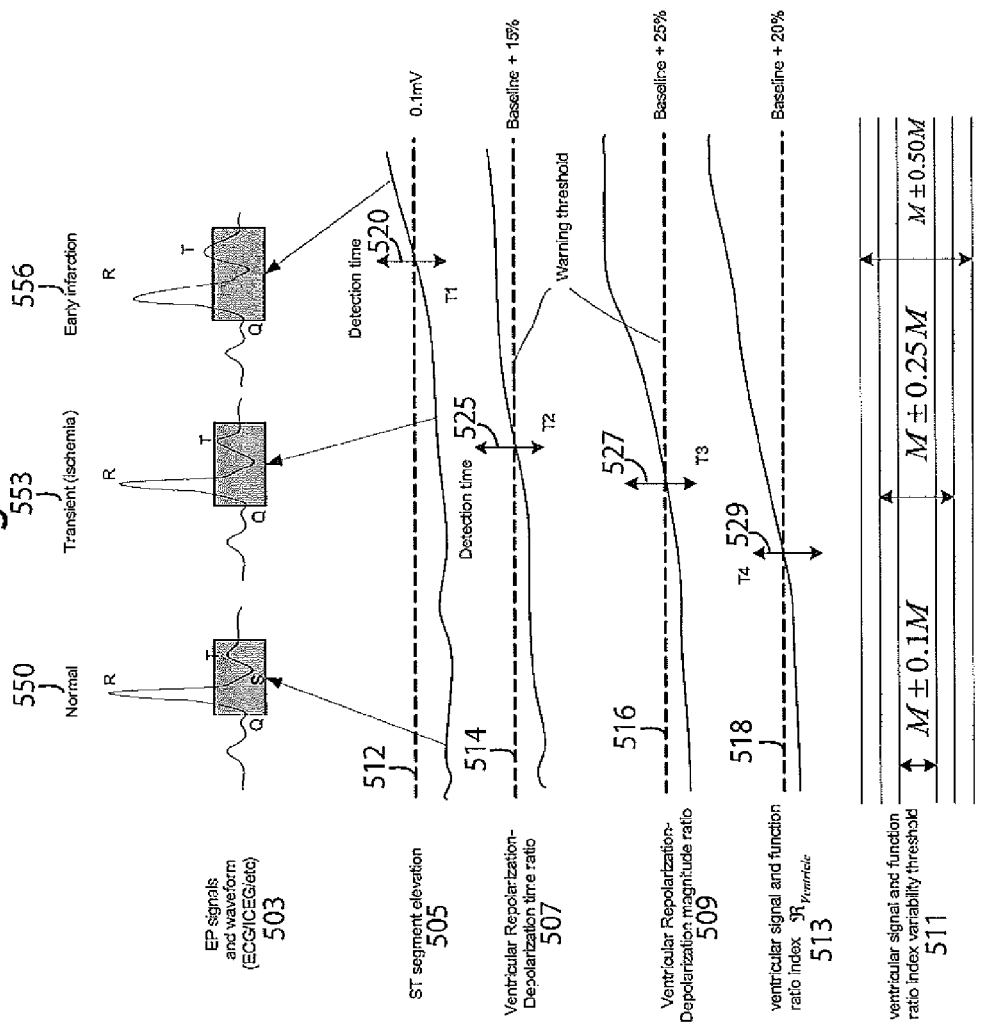

SYSTEM FOR CARDIAC CONDITION CHARACTERIZATION USING ELECTROPHYSIOLOGICAL SIGNAL DATA

This is a non-provisional application of provisional application Ser. No. 61/412,413 filed Nov. 11, 2010, by H. Zhang.

FIELD OF THE INVENTION

This invention concerns a system for heart performance characterization and abnormality detection by detecting time interval and voltage amplitude characteristics of an electrical signal indicating electrical activity of a patient heart over one or more heart beat cycles.

BACKGROUND OF THE INVENTION

Myocardial ischemia and infarction analysis and recognition are needed for the management of cardiac disorders and irregularities, which may be caused by a lack of blood and oxygen in the heart tissue and cells. Usually, surface ECG (electrocardiogram) signal analysis based on waveform morphology and time domain parameters is used for myocardial ischemia and infarction detection and characterization, such as of ST segment or T wave changes (repolarization). However known systems lack efficient quantitative methods for myocardial status detection and characterization, including determination of severity and quantitative characterization of ongoing myocardial ischemia events with chest pain. Additionally, known systems for cardiac ischemia and infarction identification and analysis using ECG signals are subjective and need extensive expertise for accurate pathology interpretation, proper cardiac rhythm management and early detection of myocardial ischemia.

CAD (Coronary Artery Disease) and heart-related problems and cardiac arrhythmias are often fatal. A 12-lead electrocardiogram (ECG) and multi-channel intra-cardiac electrograms (ICEG) are a diagnostic reference standard for evaluating cardiac rhythm and events. Known waveform morphologies and time domain parameter analysis, such as of a P wave, QRS complex, ST segment and T wave, are used for cardiac arrhythmia monitoring and identification, e.g., of atrial fibrillation (AF), myocardial ischemia (MI) and ventricular tachycardia/fibrillation (VT/NT). Known system signal calculation and related analysis usually fails to localize a malfunction and identify a harmful trend of cardiac events (e.g. in myocardial ischemia and infarction), such as cardiac pathology irregularity stages and arrhythmia occurrence.

Inaccurate and subjective ECG and ICEG evaluation and diagnosis may impede cardiac rhythm management and emergency treatment. Known clinical diagnosis for myocardial ischemia and infarction detection are based on ST segment voltage deviation for ischemia event detection (e.g., 0.1 mV elevation of ST segment is a clinical standard used for myocardial ischemia (MI) detection). However this standard only works for surface ECG signals and not for intra-cardiac electrograms (ICEG signals) and an ST segment deviation (voltage) cannot be utilized as a quantitative method for myocardial ischemia severity diagnosis and characterization.

Known clinical methods for myocardial ischemia event detection and evaluation rely on a repolarization procedure and identifying ST segment and T wave morphology changes, for example. Further known clinical methods for myocardial ischemia event diagnosis fail to combine diagnosis of both the depolarization and repolarization procedures, especially the timing, frequency and energy changes of the procedures. Known methods for MI analysis focus on an event and qualitative detection and evaluation of MI occurrence and ischemia event detection systems may cause false alarms due to single parameter analysis, such as analysis involving magnitude of ST segment measurement. A system according to invention principles addresses these deficiencies and elated problems.

SUMMARY OF THE INVENTION

A system analyzes cardiac electrophysiological signals (including surface ECG signals and internal cardiac electrograms, ICEG signals) based on signal ratios of ventricular signals of different stages within a cardiac cycle to identify cardiac disorders, differentiate cardiac arrhythmia irregularities, quantitatively characterize pathological severity, and potentially predict life-threatening events. A system for heart performance characterization and abnormality detection includes an interface for receiving signal data representing an electrical signal indicating electrical activity of a patient heart over multiple heart beat cycles. A signal processor uses the received signal data in calculating at least one of, (a) a first signal characteristic value substantially comprising a ratio of a time interval from S wave to T wave, to a time interval from Q wave to S wave and (b) a second signal characteristic value substantially comprising a ratio of a T wave base voltage from a peak of a T wave to a zero base reference voltage, to an R wave base voltage from a peak of an R wave to a zero base reference voltage. A comparator compares at least one of the first and second characteristic values with a threshold value to provide a comparison indicator. A patient monitor in response to the comparison indicator indicating a calculated signal characteristic value exceeds the threshold value, generates an alert message associated with the threshold.

BRIEF DESCRIPTION OF THE DRAWING

FIG. 3 shows a Table indicating functions associated with the cardiac cycle signal parameters of FIG. 2, according to invention principles.

FIG. 4 shows a flowchart of a process for ventricle associated signal analysis and detection of myocardial ischemia, according to invention principles.

FIG. 5 illustrates ventricular depolarization and repolarization signal analysis using different methods based on ventricular waveform morphology, parameter and ratio analysis and characterization for myocardial ischemia detection, according to invention principles.

DETAILED DESCRIPTION OF THE INVENTION

Figure 1:
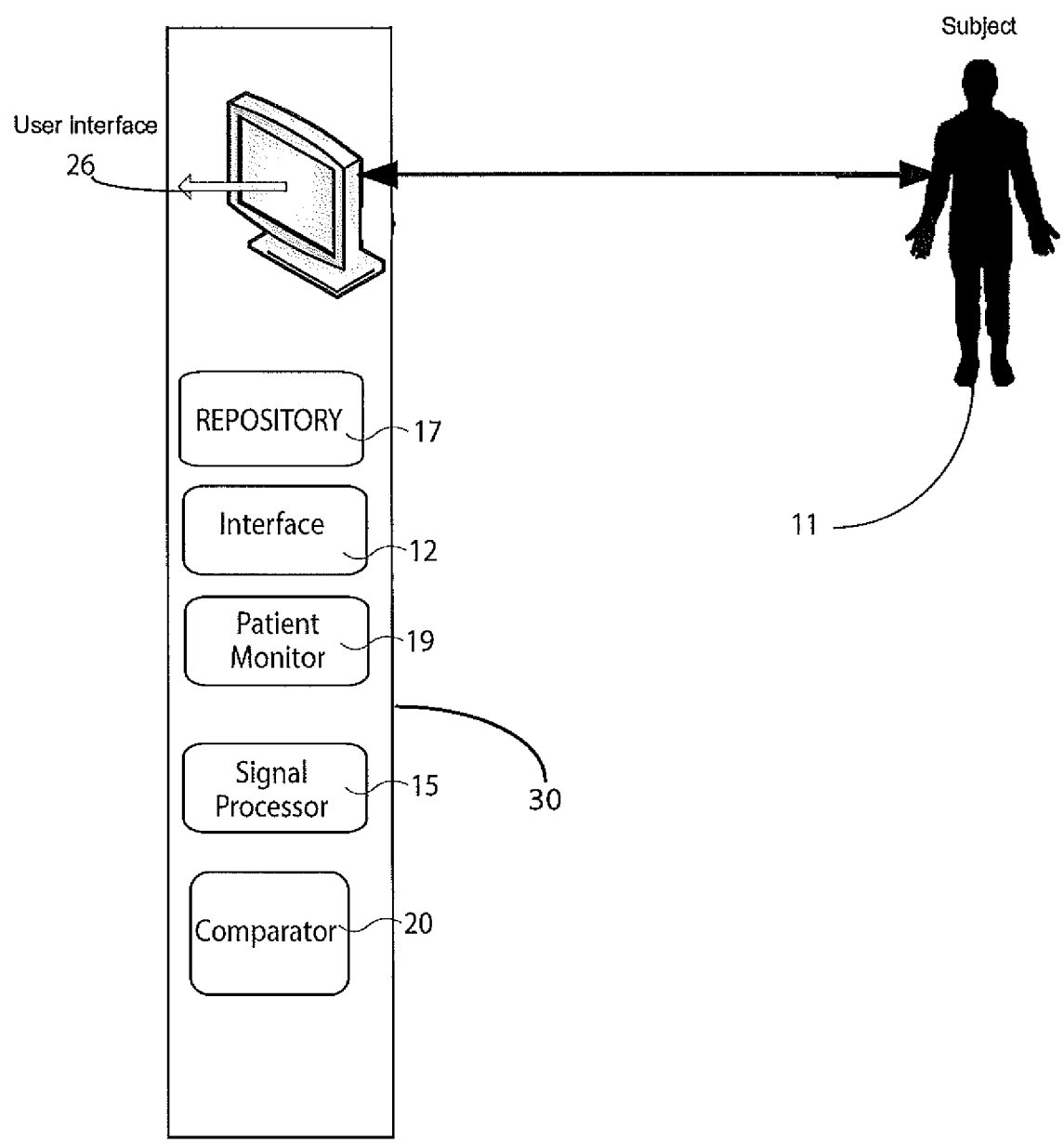
FIG. 1 shows a system for heart performance characterization and abnormality detection, according to invention principles.

A system analyzes cardiac electrophysiological signals (including surface ECG signals and internal cardiac electrograms, MEG signals) using signal ratios of ventricular signals of different stages within a cardiac cycle to identify cardiac disorders, differentiate cardiac arrhythmia irregularities, quantitatively characterize pathological severity, and potentially predict life-threatening events. The system employs advantageous signal parameter ratios associated with ventricular depolarization and repolarization procedures for cardiac signal diagnosis and evaluation. The system is used in myocardial ischemia and infarction analysis, diagnosis and characterization. The system performs signal ratio measurement and calculation including comparison of cardiac signal magnitude voltage and time duration characteristics of ventricular depolarization and repolarization signals, such as of a QRS complex and T wave within the same heart beat, for real time monitoring and analysis and detection of different ventricular arrhythmias, such as ventricular tachycardia and fibrillations.

The principal manifestations of CAD are coronary artherosclerosis (hardening of the coronary arteries) or stenosis (narrowing of the arteries), both of which ultimately force a reduction in the coronary circulation (myocardial ischemia, or infarction). During ischemia, various portions of heart muscle receive less oxygen which can ultimately lead to irreversible scarring and necrosis of the muscle tissue (myocardial infarction), reducing the efficiency with which the heart can pump blood to the rest of the body and possibly leading to fatal cardiac arrhythmias. Myocardial ischemia or infarction reduces blood flow to regions of the heart, where cells respond by altering an action potential. The changes in these individual cells manifest in the local electrograms during depolarization and repolarization, reducing signal energy (hyperkalemia or anoxia) or creating multi-phasic waveforms (decoupling). These abnormal behaviors in relatively small regions of the heart, lumped together with the rest of the heart, cause notches of small amplitude superimposed on a largely normal electrogram of both surface ECG signals and intracardiac electrograms. Ventricle area is an important pump (heart) parameter. A small ischemic region and infarction may cause severe heart arrhythmias and even death. Ventricular activity and signal monitoring of both depolarization and repolarization, may improve and expedite reliable detection of MI events.

A heart hear cycle can be divided by signals morphologies, which reflect the signals resource and myocardial activities corresponding to a P wave, QRS complex, ST segment, T wave and U wave, for example. Different portions of electrograms represent cardiac activities of a corresponding heart area and tissue. For example, a P wave is mainly associated with an atrium and may not be able to provide any information on ischemia events which occur in a ventricle, especially the left ventricle. Ventricular activities and signal morphologies are utilized by the system to diagnose the electrophysiological activities of heart tissue and ventricular function status. Within a ventricular activity of one heart beat cycle, the action potentials within a heart occur within depolarization and repolarization procedures. For ischemia and infarction monitoring and event characterization, a precise portion of an electrophysiological signal needs to be accurately extracted and analyzed.

FIG. 1 shows system 10 for heart performance characterization and abnormality detection. System 10 comprises at least one computer system, workstation, server or other processing device 30 including interface 12, repository 17, patient monitor 19, signal processor 15, comparator 20 and a user interface 26. Signal interface 12 receives and processes signals from patient 11, including respiration, vital signs, hemodynamic and electrophysiological (EP) signals that are acquired by different sensors and transducers in unit 12. The acquired signals are digitized for analysis in computer system 30. Interface 12 receives signal data representing an electrical signal indicating electrical activity of a heart of patient 11 over multiple heart beat cycles. Signal processor 15 uses the received signal data in calculating at least one of, (a) a first signal characteristic value substantially comprising a ratio of a time interval from S wave to T wave, to a time interval from Q wave to S wave and (b) a second signal characteristic value substantially comprising a ratio of a T wave base voltage from a peak of a T wave to a zero base reference voltage, to an R wave base voltage from a peak of an R wave to a zero base reference voltage. Comparator 20 compares at least one of the first and second characteristic values with a threshold value to provide a comparison indicator. Patient monitor 19 in response to the comparison indicator indicating a calculated signal characteristic value exceeds the threshold value, generates an alert message associated with the threshold.

Figure 2:
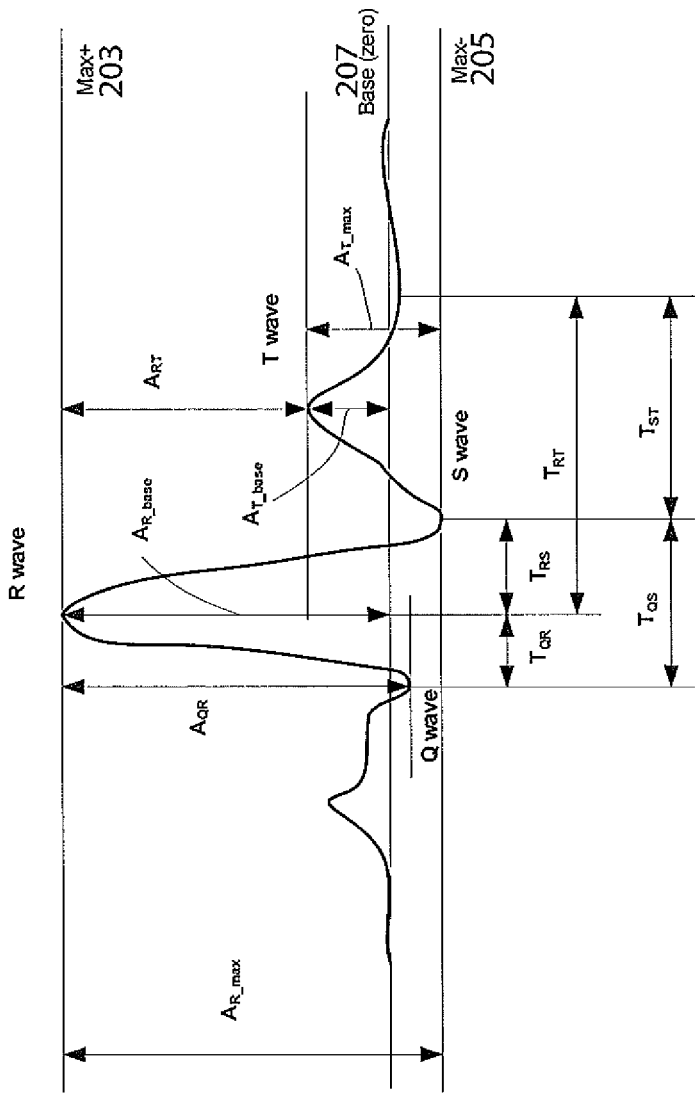
FIG. 2 shows a signal representing a cardiac cycle indicating signal parameters and ventricular repolarization and depolarization portions, according to invention principles.

FIG. 2 shows a signal representing a cardiac cycle indicating signal parameters and ventricular repolarization and depolarization portions used in ischemia detection and myocardial ischemia information extraction and characterization. In one embodiment system 10 (FIG. 1) focuses on examination of ventricular activities and morphologies. A QRS complex portion represents ventricular contraction (ventricular depolarization). A T wave portion (from an S wave to the end of a T wave portion) represents ventricular repolarization. System 10 compares the ventricular depolarization and repolarization electrophysiological activities to detect and characterize myocardial ischemia events, for example. Ventricular activities are associated (based on cardiac signal morphology) with, Q wave, R wave, S wave and T wave. In the time domain, these waves are differently identified based on the functions (as described in the table of FIG. 3). In FIG. 2 Max+ 203 comprises a maximum peak magnitude voltage of a whole heart cycle (e.g. R wave) while Max− 205 is a minimum magnitude voltage of the heart cycle (e.g. S wave). Further, Base (zero) 207 is a zero baseline voltage (0 V, voltage reference).

FIG. 3 shows a Table indicating functions associated with the ventricular depolarization and repolarization related cardiac cycle signal parameters of FIG. 2. The Table lists time domain waveform parameters in column 303 and related function description in column 305. The parameters include $A_{R-max}$ 307, $A_{R-base}$ 309, $A_{T-base}$ 311, $A_{QR}$ 313, $A_{RT}$ 315, $A_{T-max}$ 317, $T_{QR}$ 319, $T_{RS}$ 321, $T_{RT}$ 323, $T_{QS}$ 325 and $T_{ST}$ 327 that are described in corresponding rows of column 305. System 10 (FIG. 1) derives and uses a single parameter of the Table to determine heart status of a patient including status of ventricular electrophysiological activities. The Table parameters are also used in combination to track and capture waveform and cardiac function changes. For example, system 10 quantitatively diagnoses and characterizes myocardial ischemia by comparing ventricular repolarization and depolarization time durations $T_{ST}$ 327 with $T_{QS}$ 325. A small portion of ventricular tissue and only one of the ventricular procedures such as the fast depolarization or slow depolarization or repolarization procedures may be affected during an early stage of a myocardial ischemia event. The remaining ventricular procedures are usually stable, hence the system advantageously provides early detection, localization and severity determination of a myocardial ischemic event by comparison of different portions of a cardiac cycle signal representing ventricular activities.

In one embodiment, the system calculates different parameter ratios including,
Ventricular Repolarization-Depolarization time ratio:

$$\text{Ratio\_1} = \frac{T_{ST}}{T_{QS}};$$

Ventricular Repolarization-Depolarization magnitude ratio:

$$\text{Ratio\_2} = \frac{A_{T\_base}}{A_{R\_base}} \quad \text{or} \quad \text{Ratio\_3} = \frac{A_{T\_max}}{A_{R\_max}};$$

Ventricular fast versus slow Depolarization time ratio:

$$\text{Ratio\_4} = \frac{T_{QR}}{T_{RS}}$$

Ventricular fast versus slow Depolarization magnitude ratio:

$$\text{Ratio\_5} = \frac{A_{QR}}{A_{R\_max}}$$

or $$\text{Ratio\_6} = \frac{A_{QR}}{A_{R\_base}};$$

Ventricular fast Depolarization versus Repolarization time ratio:

$$\text{Ratio\_7} = \frac{T_{QR}}{T_{ST}}$$

Ventricular fast Depolarization versus Repolarization magnitude ratio:

$$\text{Ratio\_8} = \frac{A_{QR}}{A_{T\_base}} \quad \text{or} \quad \text{Ratio\_9} = \frac{A_{QR}}{A_{T\_max}};$$

Ventricular slow Depolarization versus Repolarization time ratio:

$$\text{Ratio\_10} = \frac{T_{RS}}{T_{ST}}$$

Or $$\text{Ratio\_11} = \frac{T_{RS}}{T_{RT}}$$

Ventricular slow Depolarization versus Repolarization magnitude ratio:

$$\text{Ratio\_12} = \frac{A_{R\_max} - A_{R\_base}}{A_{T\_base}}$$

System 10 calculates and uses other ratios to localize and characterize ventricular activity changes, including: 1) a ratio indicating a ventricular fast depolarization portion time duration relative to the remainder of ventricular time duration; 2) the time duration of ventricular activities, from Q wave to the end of the successive subsequent T wave and 3) a ventricular fast depolarization portion time duration relative to a whole ventricular activity time duration. In an embodiment, a user or system adaptively selects parameters and ratios, or a parameter and/or ratio combination for patient heart signal monitoring, e.g., in an ICD (intra-cardiac device) patient. An ICD device adaptively selects a calculation based on a catheter or ECG lead position, signal resources and pre-configuration data.

System 10 uses ventricular morphology indicative parameters for monitoring and analyzing real time cardiac signals and functions. System 10 improves detection and diagnosis of myocardial ischemia events by use of multiple parameters in combination for ventricular function analysis. In response to a small change in ischemic tissue of a ventricle (e.g. the left ventricle) muscle, the ventricular depolarization and repolarization procedures are prolonged. As a result typically corresponding ratios associated with depolarization and repolarization show significant differences and the system employs a multiple parameter ventricular activity function ratio including, Ventricular Repolarization-Depolarization signal change indicative ratio:

$$\text{Ratio\_13} = \frac{A_{R\_max}/(T_{QR} + T_{RS})}{A_{T\_max}/T_{ST}}$$

Or $$\text{Ratio\_14} = \frac{A_{R\_base}/(T_{QR} + T_{RS})}{A_{T\_base}/T_{ST}}$$

Ventricular fast-slow Depolarization signal change indicative ratio:

$$\text{Ratio\_15} = \frac{A_{QR}/T_{QR}}{A_{R\_max}/T_{RS}}$$

System 10 selects and calculates ratios and parameters used in morphology detection based on type of clinical application, to detect signal changes and for signal comparison such as comparison of fast ventricular depolarization with. Repolarization and ventricular repolarization with Repolarization or determination of signal expansion ratio due to ischemia.

In complex clinical cases, one parameter may not provide a stable and sensitive diagnosis in real time cases in which cardiac signals may be corrupted by substantial noise. Hence, in order to improve reliability and sensitivity of morphology detection, ratios (user or system selected ratios) are combined to derive a final ventricular signal and function ratio index $\Re_{Ventricle}$:

ventricular signal and function ratio:

$$\Re_{Ventricle} = \sum_{i \in Ratio\ selection} \mu_i Ratio_i$$

where, i is the number of the ratio selected for the calculation of the ventricular signal and function ratio; $Ratio_i$ is the ratio of cardiac signal waveform morphology and activity; $\mu_i$ is the weight for each ratio in the combination and $\mu_i$ may be adaptively selected by the system or be predetermined and ratio specific and time varying, such as $\mu_i(t)$, which can be adaptively updated and controlled by a user or system 10. $\Re_{Ventricle}$ function ratio value is utilized by system 10 for ventricular ischemia event detection and characterization, such as ischemia event occurrence, ischemia event severity, and is used to predict a critical time of an infarction event and suggest candidate treatment (such as medicine and treatment time). An $\Re_{Ventricle}$ calculation is used for cardiac function (such as atrial function) signal analysis and other patient signal analysis (such as SPO2, respiration, O2 and blood pressure signals).

System 10 also employs statistical evaluation methods to quantify and characterize change by calculating standard deviation, variation and variability used for severity and ischemia level determination. The system uses the following functions for ventricular parameter and ratio calculation and variation determination.

Mean or averaging value (expectation);

$$\text{mean}(X) = \frac{1}{N} \sum_{i \in N} X(i);$$

Standard deviation:

$$STD(X) = \frac{1}{N-1} \sum_{i \in N-1} (X(i) - \text{mean}(X))$$

$$\text{Signal Variation} = \frac{\text{mean}(X)}{STD(X)}$$

$$\text{Signal Variability} = \frac{\max(X - \text{mean}(X))}{\text{mean}(X)}$$

In which, X is a time or magnitude ratio measurement or a value derived by calculation as previously described; N is a calculation window size (there are N cycles in a shifting calculation window).

FIG. 4 shows a flowchart of a process performed by system 10 (FIG. 1) for ventricle associated signal analysis and detection of myocardial ischemia. Interface 12 in step 408 provides sampled heart activity data by buffering and digitizing an electrical signal (such as an ECG or ICEG signal) received in step 406 and indicating electrical activity of a patient heart over multiple heart cycles. Interface 12 filters the sampled data using a filter for attenuating power line noise and patient movement noise. The filter is adaptively selected in response to data indicating clinical application (e.g. ischemia detection application, rhythm analysis application). In step 414, signal processor 15 identifies heart cycles (RR cycles) and in step 416 identifies different segments (QRS, ST, P wave, Q wave, R wave, S wave, ST segment, T wave, U wave segments, for example) of the filtered sampled data signal and determines times $T_{QR}$, $T_{RS}$, $T_{RT}$, $T_{QS}$ and $T_{ST}$ as shown in FIG. 3. In step 418, signal processor 15 measures the voltage amplitudes of the filtered sampled data of the Table of FIG. 3 including $A_{R-max}$, $A_{R-base}$, $A_{T-base}$, $A_{QR}$, $A_{RT}$ and $A_{T-max}$.

Signal processor 15 uses a peak detector and time detector for identifying the peaks and detecting a time difference between the identified peaks. Signal processor 15 measures the times and voltage amplitudes in the filtered sampled data by detecting peaks of ECG and ICEG waveforms within received sampled data by synchronization of a heart electrical activity waveform and peak detection of a wave using a known peak detector and by identifying peaks of other waves by segmenting the signal represented by the sampled data into windows where the waves are expected and identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

In step 420, signal processor 15 uses the voltage amplitude and time values determined in steps 416 and 418 in calculating the fifteen ratios, Ratio_1 to Ratio_15 as previously described as well as ventricular signal and function ratio $\Re_{Ventricle}$. Signal processor 15 calculates the ratios for filtered sampled data from multiple different cardiac sites acquired by multiple catheter leads of a multichannel (e.g., basket) type catheter, for example. In step 422, signal processor 15 analyzes the multichannel signals to determine particular impaired cardiac tissue areas. Calculations and measurements of signals from different catheter channel leads may have different sensitivities. Processor 15 in step 425 analyzes the multiple measured parameters of the Table of FIG. 3 and the fifteen ratios, Ratio_1 to Ratio_15 by performing a statistical analysis and calculating mean or average value, standard deviation, signal variation and signal variability using the functions previously described.

In step 426 signal processor 15 employs mapping information, associating ranges of the measured parameters of the Table of FIG. 3 and the fifteen ratios, Ratio_1 to Ratio_15, with corresponding medical conditions (e.g., ischemia) in determining patient medical conditions, events and patient health status. If signal processor 15 and comparator 20 in step 426 determine a medical condition indicating cardiac impairment or another abnormality is identified, processor 15 in step 435 uses the mapping information in determining severity, type and location of a cardiac condition. Patient monitor 19 in step 437 generates an alert message identifying the medical condition and abnormality and communicates the message to a user and stores data indicating the identified condition and associated calculated parameters in repository 17. Processor 15 also determines the severity and location of the condition.

Processor 15 in step 423 selects a signal channel of a multi-channel catheter for use as signal input and adaptively adjusts the number of heart cycles in a calculation window used for averaging and adjusts the selected portions and ROI of a filtered signal analyzed and adjusts a threshold employed by comparator 20 to improve medical condition detection. In the analysis, processor 15 selects a severity threshold, calculation time step, monitored tissue location in response to user command or automatic system adaptive adjustment. The multi-channel patient signals include different lead signals or surface ECG signals or different channels (unipolar or bipolar) ICEG signals. If signal processor 15 and comparator 20 in step 426 do not identify a medical condition, the process is repeated from step 408. System 10 identifies and monitors different kinds of clinical events and cardiac pathology using the measured calculated parameters and ratios.

FIG. 5 illustrates ventricular depolarization and repolarization signal analysis using different methods based on ventricular waveform morphology, parameter and ratio analysis and characterization for myocardial ischemia detection. The system 10 (FIG. 1) ventricular depolarization and repolarization parameter and ratio analysis is utilized to monitor and diagnose different kinds of clinical event and cardiac pathologies in a ventricle, such as myocardial ischemia, myocardial infraction, ventricular tachycardia and ventricular fibrillation. FIG. 5 shows an example, of simulated left ventricular ischemia data analysis involving normal 550, transient 553 and early infarction 556 stages of an EP (electrophysiological) signal waveform 503. Processor 15 calculates and plots different types of parameter including, standard ST segment elevation 505, a ventricular repolarization-depolarization ratio 507, a ventricular repolarization-depolarization magnitude ratio 509 and a ventricular signal and function ratio $\Re_{Ventricle}$ 513 that are used for comparison and detection of time and ischemia event severity. System 10 adaptively determines thresholds based on baseline normal parameter values and warning value levels to detect small changes within a ventricular waveform and associated trends.

The ST segment elevation waveform 505 exceeds the detection threshold of 0.1 mV 512 at time T1 identifying myocardial ischemia (at this time, it may be in an early stage of myocardial infarction). Processor 15 selects ventricular Repolarization-Depolarization time and magnitude ratios 507 and 509 for use in detection. Processor 15 adaptively selects warning thresholds baseline+15% 514 and baseline+25% 516 separately in response to type of clinical application. With these two ratios, the myocardial ischemia is detected at T2 525 and T3 527 during the abnormal phase 553, which is about 25 and 30 seconds earlier than the ST segment detection in phase 556. Signal processor 15 calculates ventricular signal and function ratio index $\Re_{Ventricle}$ 513 by combining different ratios with different weights (the weights are determined in response to significance of individual ratios in the application. An artificial neural network can be utilized to train and derive the best weight coefficient set.). With $\Re_{Ventricle}$ calculation (the threshold adaptively selected to be baseline+20% 518), the myocardial ischemia event is detected at T4 529, which is about 45 second earlier than the ST segment analysis in phase 556. The thresholds in the analysis may be determined by a user or adaptively automatically by the system.

Processor 15 uses a 10 heart beat window size for averaging to obtain a mean and standard deviation value for use in determining variation and variability of timing and magnitude ratios. Normal signals are used as a reference and as a baseline. Processor 15 continuously performs real time calculations using reference signal values and sets a normal signal based calculated value to "1". Patient monitor 19 outputs a warning to a user and system 10 identifies a treatment in response a real time calculated value (normalized) being higher or lower (indicating variation, such as 0.775 for a depolarization to repolarization timing ratio, e.g. due to myocardial ischemia) than the normal value "1". A+/−20% threshold 518 from the normalized reference value is applied to a ventricular signal and function ratio index $\Re_{Ventricle}$, for example. Variability thresholds 511 of 0.1, 0.25 and 0.5 of the maximum value of the $\Re_{Ventricle}$ calculated value are adaptively selected and used in the three phases 550, 553 and 556. The severity of ongoing ventricular functions and tissues is indicated by calculated ratios and predetermined warning thresholds. For example threshold value (e.g. 20%) is 10 for detection of myocardial ischemia and normal is 0 (normal). A 10% change of the ratio indicates severity 5. The higher a severity index value, the more severe and critical is the patient ventricular function abnormality.

A calculation may be utilized independently. For example, signal magnitude and duration parameters or ratios, may be used in an implantable cardiac device, which advantageously use low complexity calculation methods. The system identifies cardiac disorders, differentiates cardiac arrhythmias, characterizes pathological severity, predicts life-threatening events, and improves heart medical treatment, such as drug delivery and long term cardiac treatment (e.g., using bedside cardiac monitoring or portable patient cardiac function monitoring and analysis such as via Holster Monitoring). Different ratios are utilized to track and monitor patient status for detecting MI events. At the beginning of the monitoring, one or multiple ratios may be used, such as depolarization to repolarization timing ratio. A 5-10 heart cycle averaging data window may be used for calculation and monitoring, such as 5-8 hear beat window and a threshold can be setup at 15% which may be initially low. Once an MI event is detected, more ratios and calculations may be utilized for more accurate detection and to reduce false alarms. At this stage, a larger calculation window such as 8-15 heart cycles may be used and a warning and alarm threshold may be set higher to 20%. This method improves detection of an MI event and reduces the rate of false alarms.

Figure 6:
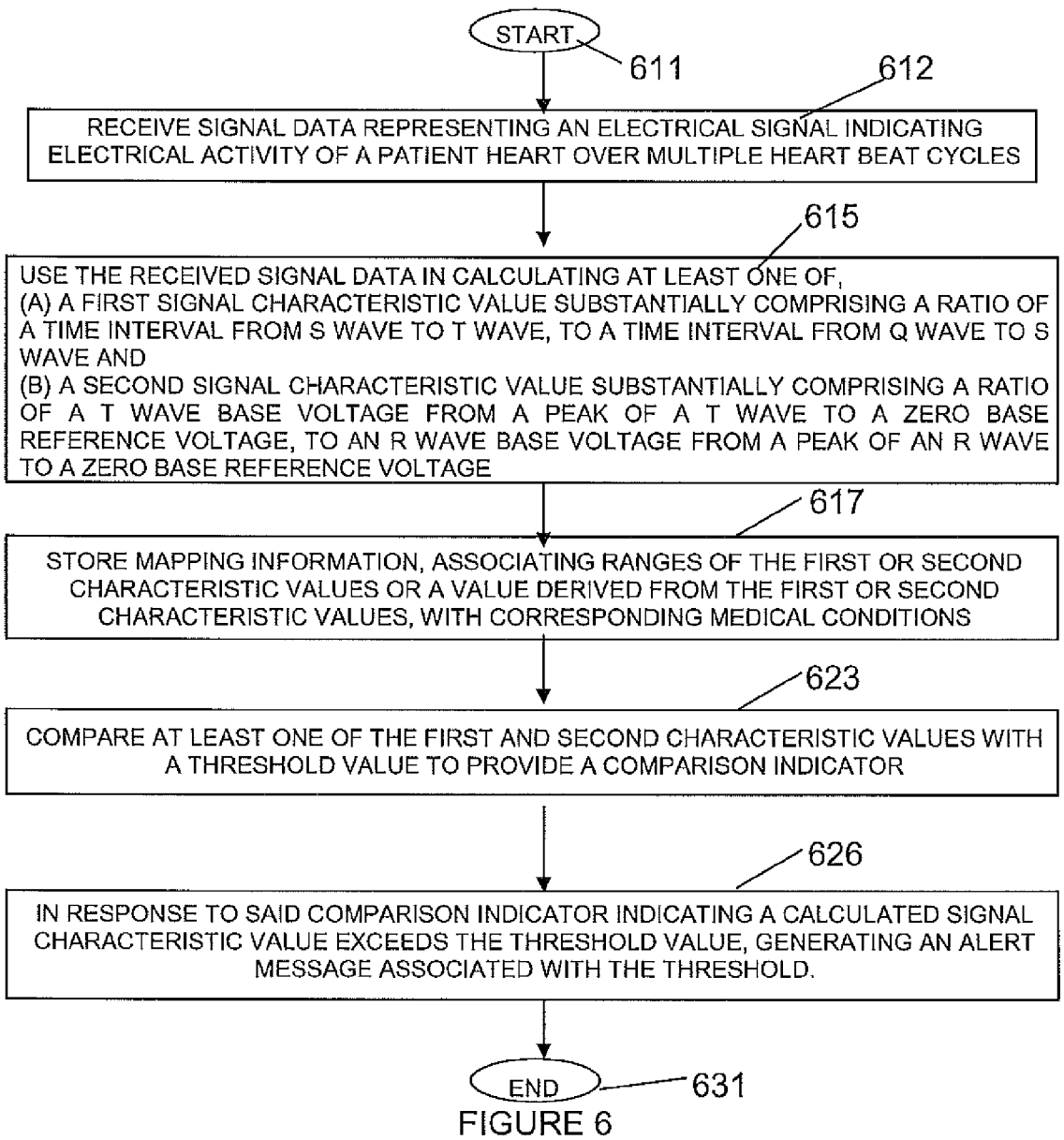
FIG. 6 shows a flowchart of a process used by a system for heart performance characterization and abnormality detection, according to invention principles.

FIG. 6 shows a flowchart of a process used by a system for heart performance characterization and abnormality detection. In step 612 following the start at step 611 interface 12 receives signal data such as digitally sampled data representing an electrical signal indicating electrical activity of a patient heart over multiple heart beat cycles. Signal processor 15 in step 615 uses the received signal data in calculating at least one of (a) a first signal characteristic value substantially comprising a ratio of a time interval from S wave to T wave, to a time interval from Q wave to S wave and (b) a second signal characteristic value substantially comprising a ratio of a T wave base voltage from a peak of a T wave to a zero base reference voltage, to an R wave base voltage from a peak of an R wave to a zero base reference voltage. The time interval occurs in one embodiment occurs within a single heart cycle. Signal processor 15 processes the received signal data to calculate at least one of, (i) a third signal characteristic value substantially comprising a ratio of a maximum magnitude (peak to peak) voltage value for a T wave, to a maximum magnitude (peak to peak) voltage value for an R wave and (ii) a fourth signal characteristic value substantially comprising a ratio of a time interval from a Q wave to an R wave, to a time interval from an R wave to and S wave and In one embodiment, signal processor 15 processes the received signal data to calculate a third signal characteristic value substantially comprising, $$\text{ratio} = \frac{A_{R\_max}/(T_{QR} + T_{RS})}{A_{T\_max}/T_{ST}}$$

where, $A_{R\_max}$ is substantially maximum magnitude (peak to peak) voltage value for an R wave, $T_{QR}$ is substantially a time interval from Q wave to R wave, $T_{RS}$ is substantially a time interval from an R wave to an S wave, $A_{T\_max}$ is substantially a maximum magnitude (peak to peak) voltage value for a T wave and $T_{ST}$ is substantially a time interval from S wave to T wave. Signal processor 15 also processes the received signal data to calculate a weighted sum of different calculated ratios of parameters derived from the received signal and individual weights of the weighted sum are at least one of adaptively controlled by processor 15 and time varying. The weighted sum of different calculated ratios of parameters is of the form, $$\sum_{i \in \text{Ratio selection}} \mu_i Ratio_i.$$

Signal processor 15 calculates a standard deviation of the first or second signal characteristic value ratio over multiple heart cycles and calculates a signal variability of the time intervals determined over multiple heart cycles. The signal variability is calculated over multiple heart cycles and is of the form, $$\text{Signal Variability} = \frac{\max(X - \text{mean}(X))}{\text{mean}(X)}$$

where X is the first or second signal characteristic value ratio.

Signal processor 15 in step 617 stores predetermined mapping information in repository 17, associating ranges and threshold values of the first or second characteristic values with corresponding medical conditions. In step 623, comparator 20 compares the first, second, third and fourth characteristic values with the ranges and a threshold value to provide a comparison indicator identifying a medical condition. The threshold value is derived from recorded electrical signal data for the patient or a population of patients having similar demographic characteristics to the patient including at least two of, (a) age, (b) weight, (c) gender and (d) height, to those of the patient. Signal processor 15 dynamically adjusts the threshold value in response to a determined sensitivity of arrhythmia detection. Patient monitor 19 in step 626 in response to the comparison indicator indicating a calculated signal characteristic value, calculated signal variability value or a calculated standard deviation value exceeds the threshold value, generates an alert message identifying the medical condition. The predetermined mapping information associates ranges of the first or second characteristic values with particular patient demographic characteristics and with corresponding medical conditions and the system uses patient demographic data including at least one of, age weight, gender and height in comparing the ratio with the ranges and generating an alert message indicating a potential medical condition. The process of FIG. 6 terminates at step 631.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system analyzes cardiac electrophysiological signals by performing signal ratio measurement and calculation including comparison of cardiac signal magnitude voltage and time duration of ventricular depolarization and repolarization signals, such as a QRS complex, T wave within the same heart beat, for real time monitoring and analysis. Further, the processes and applications may, in alternative embodiments, be located on one or more (e.g., distributed) processing devices on a network linking the units of FIG. 1. Any of the functions and steps provided in FIGS. 1-6 may be implemented in hardware, software or a combination of both.

What is claimed is:

1. A system comprising:
   an interface configured to receive signal data representing an electrical signal indicating electrical activity of a patient heart over a plurality of heart beat cycles;
   a signal processor for configured to:
      determine a time interval from an S wave to a T wave based on the signal data;
      determine a time interval from a Q wave to an S wave based on the signal data;

calculate a first comparison value comparing the time interval from the S wave to the T wave to the time interval from the Q wave to the S wave; and determine a cardiac condition based on the first comparison value; and a patient monitor configured to, in response to said determination of the cardiac condition, generate an alert message associated with the cardiac condition.

2. A system according to claim 1, wherein
the time interval from the S wave to the T wave and the time interval from the Q wave to the S wave occur within a single heart cycle.

3. A system according to claim 1, wherein
said signal data is digitally sampled data.

4. A system according to claim 1, wherein
said signal processor is further configured to determine, based on the received signal data, a second comparison value comparing a maximum magnitude (peak to peak) voltage value for a T wave to a maximum magnitude (peak to peak) voltage value for an R wave and a third comparison value comparing a time interval from a Q wave to an R wave to a time interval from an R wave to and S wave, and wherein said signal processor is further configured to determine the cardiac condition based on the first comparison value, the second comparison value and the third comparison value.

5. A system according to claim 1, wherein
said signal processor is further configured to calculate from the received signal data a signal characteristic value comprising, $$\text{ratio} = \frac{\frac{A_{R\_max}}{(T_{QR} + T_{RS})}}{\frac{A_{T\_max}}{T_{ST}}}$$

where, $A_{R\_max}$ is substantially maximum magnitude (peak to peak) voltage value for an R wave, $T_{QR}$ is substantially a time interval from Q wave to R wave, $T_{RS}$ is substantially a time interval from an R wave to an S wave, $A_{T\_max}$ is substantially a maximum magnitude (peak to peak) voltage value for a T wave and $T_{ST}$ is substantially a time interval from S wave to T wave.

6. A system according to claim 1, wherein
said signal processor is configured to calculate a weighted sum of different calculated ratios of parameters derived from the received signal.

7. A system according to claim 6, wherein
individual weights of said weighted sum are at least one of,
(a) adaptively controlled by a processor and
(b) time varying.

8. A system according to claim 6, wherein
said weighted sum of different calculated ratios of parameters is of the form, $$\sum_{i \in \text{Ratio selection}} \mu_i Ratio_i$$

wherein $Ratio_i$ is the i-th calculated ratio, and $\mu_i$ is a weight associated with the i-th calculated ratio.

9. A system according to claim 1, wherein
the determination of the cardiac condition based on the first comparison value comprises comparing the first comparison value to a threshold value,
wherein said signal processor is configured to derive said threshold value from recorded electrical signal data for said patient.

10. A system according to claim 1, wherein
the determination of the cardiac condition based on the first comparison value comprises comparing the first comparison value to a threshold value,
wherein said signal processor is configured to derive said threshold value from recorded electrical signal data for a population of patients.

11. A system according to claim 10, wherein
said population of patients has similar demographic characteristics including at least two of, (a) age, (b) weight, (c) gender and (d) height, to those of said patient.

12. A system according to claim 1, wherein
the determination of the cardiac condition based on the first comparison value comprises comparing the first comparison value to a threshold value,
wherein said signal processor is configured to dynamically adjust said threshold value in response to a determined sensitivity of arrhythmia detection.

13. A system according to claim 1, wherein
said signal processor is configured to:
calculate a standard deviation of said first comparison value over a plurality of heart cycles, and
determine the cardiac condition based on the standard deviation of the first comparison value.

14. A system according to claim 1, wherein
said signal processor is configured to:
calculate a signal variability of said time intervals determined over a plurality of heart cycles and
determine the cardiac condition based on the signal variability and the first comparison value.

15. A system according to claim 14, wherein
said signal variability is calculated over a plurality of heart cycles and is of the form, $$\text{Signal Variability} = \frac{\max(X - \text{Mean}(X))}{\text{Mean}(X)}$$

where X is said first comparison value.

16. A system according to claim 1, including
a repository of predetermined mapping information, associating ranges of the first comparison value with corresponding medical conditions, wherein
said cardiac condition is determined based on the first comparison value and the predetermined mapping information.

17. A system according to claim 16, wherein
said predetermined mapping information associates ranges of the first comparison value with particular patient demographic characteristics and with corresponding medical conditions, and said system is configured to use patient demographic data including at least one of age weight, gender and height in comparing the first comparison value with said ranges.

18. A system according to claim 1, wherein said signal processor is further configured to determine, based on the received signal data, a second comparison value comparing a T wave base voltage from a peak of a T wave to a zero base reference voltage, to an R wave base voltage from a peak of an R wave to a zero base reference voltage, wherein said signal processor is further configured to determine the cardiac condition based on the first comparison value and the second comparison value.

19. A method comprising:

receiving signal data representing an electrical signal indicating electrical activity of a patient heart over a plurality of heart beat cycles;

determining a time interval from an S wave to a T wave based on the signal data;

determining a time interval from a Q wave to an S wave based on the signal data;

calculating a first comparison value comparing the time interval from the S wave to the T wave to the time interval from the Q wave to the S wave; and determining a cardiac condition based on the first comparison value in response to said determination of the cardiac condition, generating an alert message associated with the cardiac condition.

* * * * *